(12) United States Patent
Mori et al.

(10) Patent No.: US 10,411,059 B2
(45) Date of Patent: Sep. 10, 2019

(54) IMAGING PANEL AND X-RAY IMAGING SYSTEM PROVIDED WITH SAID IMAGING PANEL

(71) Applicant: Sharp Kabushiki Kaisha, Osaka (JP)

(72) Inventors: Shigeyasu Mori, Osaka (JP); Kazuhide Tomiyasu, Osaka (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 460 days.

(21) Appl. No.: 15/321,142

(22) PCT Filed: Jun. 25, 2015

(86) PCT No.: PCT/JP2015/068305
§ 371 (c)(1),
(2) Date: Dec. 21, 2016

(87) PCT Pub. No.: WO2016/002612
PCT Pub. Date: Jan. 7, 2016

(65) Prior Publication Data
US 2017/0154916 A1 Jun. 1, 2017

(30) Foreign Application Priority Data
Jun. 30, 2014 (JP) .................................. 2014-134522

(51) Int. Cl.
*G01N 23/04* (2018.01)
*G01T 1/20* (2006.01)
(Continued)

(52) U.S. Cl.
CPC ...... *H01L 27/14663* (2013.01); *A61B 6/4216* (2013.01); *G01T 1/20* (2013.01);
(Continued)

(58) Field of Classification Search
CPC ....... A61B 6/4216; A61B 6/4233; G01T 1/20; G01T 1/24; H01L 27/14614;
(Continued)

(56) References Cited

U.S. PATENT DOCUMENTS 9,372,268 B2 * 6/2016 Kondo ..................... G01T 1/20
2004/0104351 A1   6/2004 Shibayama
(Continued)

FOREIGN PATENT DOCUMENTS

| JP | 2002-124676 A | 4/2002 |
| JP | 2006-156555 A | 6/2006 |

(Continued)

OTHER PUBLICATIONS

U.S. Appl. No. 15/320,682, filed Dec. 20, 2016.
(Continued)

*Primary Examiner* — Don K Wong
(74) *Attorney, Agent, or Firm* — ScienBiziP, P.C.

(57) ABSTRACT

An aim of the present invention is to make it possible to achieve stable operation of thin film transistors in an imaging panel of an X-ray imaging system that uses an indirect conversion scheme. An imaging panel includes a substrate, thin film transistor, photoelectric conversion element, and bias wiring line. The thin film transistor is formed on the substrate. The photoelectric conversion element is connected to the thin film transistor and irradiated by scintillation light. The bias wiring line is connected to the photoelectric conversion element and applies a reverse bias voltage to the photoelectric conversion element. The thin film transistor includes a semiconductor active layer and a gate electrode. The gate electrode is formed between the substrate and semiconductor active layer. The bias wiring (Continued)

line includes a portion that overlaps the gate electrode and semiconductor active layer as seen from the radiation direction of the scintillation light.

12 Claims, 12 Drawing Sheets

(51) Int. Cl.
    *H01L 27/146*     (2006.01)
    *H04N 5/32*     (2006.01)
    *A61B 6/00*     (2006.01)
    *H04N 5/359*     (2011.01)

(52) U.S. Cl.
    CPC .. *H01L 27/14614* (2013.01); *H01L 27/14632* (2013.01); *H01L 27/14687* (2013.01); *H04N 5/32* (2013.01); *H04N 5/359* (2013.01); *A61B 6/4233* (2013.01)

(58) Field of Classification Search
    CPC ......... H01L 27/14601; H01L 27/14612; H01L 27/14638
    See application file for complete search history.

(56) References Cited

U.S. PATENT DOCUMENTS

| | | |
|---|---|---|
| 2009/0057564 A1 | 3/2009 | Miyayama et al. |
| 2009/0078877 A1 | 3/2009 | Yaegashi et al. |
| 2009/0250699 A1 | 10/2009 | Okada |
| 2011/0133095 A1 | 6/2011 | Imai |
| 2011/0186853 A1 | 8/2011 | Terai et al. |
| 2012/0313103 A1 | 12/2012 | Yamada et al. |
| 2013/0264485 A1 | 10/2013 | Kawanabe et al. |
| 2013/0299711 A1 | 11/2013 | Mochizuki et al. |
| 2013/0307041 A1 | 11/2013 | Mochizuki et al. |
| 2014/0103347 A1 | 4/2014 | Ishino |
| 2017/0131413 A1 | 5/2017 | Tomiyasu et al. |
| 2017/0148843 A1 | 5/2017 | Mori et al. |
| 2017/0154914 A1 | 6/2017 | Tomiyasu et al. |
| 2017/0154915 A1 | 6/2017 | Tomiyasu et al. |
| 2017/0154916 A1 | 6/2017 | Mori et al. |
| 2017/0160403 A1 | 6/2017 | Tomiyasu et al. |

FOREIGN PATENT DOCUMENTS

| | | |
|---|---|---|
| JP | 2006-253481 A | 9/2006 |
| JP | 2007-103578 A | 4/2007 |
| JP | 2009-59975 A | 3/2009 |
| JP | 2009-94465 A | 4/2009 |
| JP | 2009-212120 A | 9/2009 |
| JP | 2009-252835 A | 10/2009 |
| JP | 2010-98329 A | 4/2010 |
| JP | 2011-124334 A | 6/2011 |
| JP | 2011-159908 A | 8/2011 |
| JP | 2013-16772 A | 1/2013 |
| JP | 2013219067 A | 10/2013 |
| JP | 2013-235934 A | 11/2013 |
| JP | 2013-235935 A | 11/2013 |
| JP | 2014-78651 A | 5/2014 |

OTHER PUBLICATIONS

U.S. Appl. No. 15/321,129, filed Dec. 21, 2016.
U.S. Appl. No. 15/320,704, filed Dec. 20, 2016.
U.S. Appl. No. 15/321,132, filed Dec. 21, 2016.
U.S. Appl. No. 15/321,127, filed Dec. 21, 2016.
U.S. Appl. No. 15/320,712, filed Dec. 20, 2016.
English machine translation of JP 2009-059975. (Listed by the U.S. Examiner in a PTO-892 form in the related U.S. Appl. No. 15/320,682.).

* cited by examiner

<A-A Cross Section>

<A-A Cross Section>

IMAGING PANEL AND X-RAY IMAGING SYSTEM PROVIDED WITH SAID IMAGING PANEL

TECHNICAL FIELD

The present invention relates to an imaging panel and X-ray imaging system, and more specifically to an imaging panel that generates images based on scintillation light from X-rays that have passed through a specimen, and an X-ray imaging system having this imaging panel.

BACKGROUND ART

There are X-ray imaging systems that capture images via an imaging panel having a plurality of pixels. X-ray imaging systems include direct conversion schemes and indirect conversion schemes.

In direct conversion schemes, an X-ray conversion film made of amorphous selenium (a-Se) converts incident X-rays into electric charge, for example. The converted electric charge is stored in a capacitor in the pixel. The stored electric charge is read out by operating a thin film transistor in the pixel. Image signals are generated based on the charge that is read out. Images are generated based on the image signals.

In indirect conversion schemes, a scintillator converts incident X-rays into scintillation light, for example. The scintillation light is converted to electric charge by a photoelectric conversion element in the pixel. The converted electric charge is read out by operating a thin film transistor in the pixel. Image signals are generated based on the charge that is read out. Images are generated based on the image signals.

SUMMARY OF THE INVENTION

An aim of the present invention is to make it possible to achieve stable operation of thin film transistors in an imaging panel of an X-ray imaging system that uses an indirect conversion scheme.

An imaging panel of one embodiment of the present invention is an imaging panel for generating an image in accordance with scintillation light obtained from X-rays that have passed through a specimen, the imaging panel including: a substrate; a thin film transistor on the substrate; a photoelectric conversion element connecting to the thin film transistor and receiving the scintillation light; and a bias wiring line connecting to the photoelectric conversion element and applying a reverse bias voltage to the photoelectric conversion element, and the thin film transistor includes: a semiconductor active layer; and a gate electrode between the substrate and semiconductor active layer, and the bias wiring line includes a section that overlaps the gate electrode and the semiconductor active layer as seen from a radiation direction of the scintillation light such that the reverse bias voltage is capacitively coupled to the semiconductor active layer thereunder.

An imaging panel in an embodiment of the present invention makes it possible to achieve stable operation of thin film transistors.

DETAILED DESCRIPTION OF EMBODIMENTS

Figure 1:
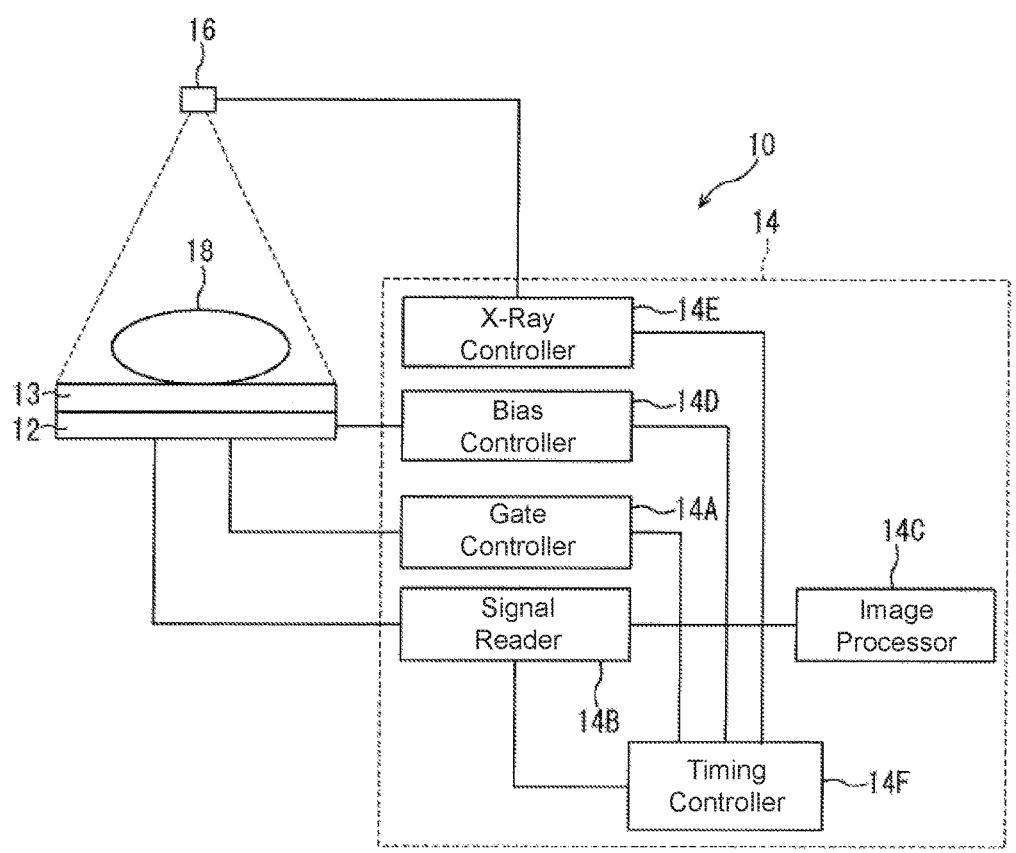
FIG. 1 is a schematic view of a general configuration of an X-ray imaging system according to Embodiment 1 of the present invention.

An imaging panel of one embodiment of the present invention is an imaging panel for generating an image in accordance with scintillation light obtained from X-rays that have passed through a specimen, the imaging panel including: a substrate; a thin film transistor on the substrate; a photoelectric conversion element connecting to the thin film transistor and receiving the scintillation light; and a bias wiring line connecting to the photoelectric conversion element and applying a reverse bias voltage to the photoelectric conversion element, and the thin film transistor includes: a semiconductor active layer; and a gate electrode between the substrate and semiconductor active layer, and the bias wiring line includes a section that overlaps the gate electrode and the semiconductor active layer as seen from a radiation direction of the scintillation light such that the reverse bias voltage is capacitively coupled to the semiconductor active layer thereunder.

In the imaging panel, it is possible for the bias wiring line to shield the semiconductor active layer from light. Thus, it is harder for scintillation light to enter the semiconductor active layer. This results in the characteristics of the thin film transistor being unsusceptible to deterioration. Accordingly, it is possible to stabilize the operation of the thin film transistor.

In the imaging panel, the bias wiring line includes a portion that overlaps the gate electrode. Therefore, it is possible to use this portion as a second gate electrode (backgate electrode). As a result, setting the voltage applied to the backgate electrode as appropriate makes it possible to modify the operating characteristics of the thin film transistor.

The thin film transistor includes a drain electrode connecting to the photoelectric conversion element, and the photoelectric conversion element includes: an n-type semiconductor layer contacting the drain electrode; an intrinsic semiconductor layer contacting the n-type semiconductor layer; and a p-type semiconductor layer contacting the intrinsic semiconductor layer, and the bias wiring line makes a potential of the p-type semiconductor layer lower than a potential of the n-type semiconductor layer.

In order to reduce OFF current (leakage current) of the thin film transistor, a negative charge is applied to the gate electrode when the thin film transistor is to be turned OFF. If this period is long, the threshold voltage of the thin film transistor will shift in the minus direction.

In the aspect described above, it is possible to shift the threshold voltage in the plus direction. By shifting the threshold voltage in the plus direction beforehand, the threshold voltage is not likely to reach the minimum value even if shifted in the minus direction, for example.

The thin film transistor includes a drain electrode connecting to the photoelectric conversion element, and the photoelectric conversion element includes: a p-type semiconductor layer contacting the drain electrode; an intrinsic semiconductor layer contacting the p-type semiconductor layer; and an n-type semiconductor layer contacting the intrinsic semiconductor layer, and the bias wiring line makes a potential of the n-type semiconductor layer higher than a potential of the p-type semiconductor layer.

In such a case, it is possible to shift the threshold voltage of the thin film transistor in the minus direction. This enables a reduction in the voltage for turning ON the thin film transistor (the voltage applied to the gate electrode).

It is preferable that the semiconductor active layer be made of an oxide semiconductor. In such a case, it is possible to achieve high resolution images. The reason for this is as follows.

In a thin film transistor where the semiconductor active layer is made of an oxide semiconductor, the ON current is approximately 20 times greater than conventional thin film transistors, and the OFF current (leakage current) is several orders of magnitude smaller than conventional thin film transistors. Because the ON current is larger, it is possible to reduce the size of the thin film transistor. Because the OFF current is smaller, it is possible to reduce the area of the storage capacitor. As a result, pixel pitch can be reduced, which allows for higher resolution.

The oxide semiconductor is an oxide containing prescribed proportions of indium (In), gallium (Ga), and zinc (Zn), for example.

The thin film transistor further includes: a first insulating film between the gate electrode and the semiconductor active layer and covering the gate electrode; and a second insulating film covering the semiconductor active layer, and the first insulating film and the second insulating film preferably include a silicon oxide film contacting the semiconductor active layer.

Silicon oxide films contain less hydrogen than silicon nitride films. Therefore, reducing the hydrogen contained in the semiconductor active layer makes it possible to prevent negative effects on the characteristics of the thin film transistor.

An X-ray imaging system of one embodiment of the present invention includes: the imaging panel; an X-ray source; and a scintillator between the X-ray source and the imaging panel.

The imaging panel described above makes it possible to stabilize the operation of the thin film transistor.

Specific embodiments of the present invention will be explained below with reference to figures. Portions in the drawings that are the same or similar are assigned the same reference characters and descriptions thereof will not be repeated.

Embodiment 1

FIG. 1 shows an X-ray imaging system 10 according to Embodiment 1 of the present invention. The X-ray imaging system 10 includes an imaging panel 12, scintillator 13, controller 14, and X-ray source 16.

In the X-ray imaging system 10, X-rays are radiated from the X-ray source 16, and X-rays that have passed through a specimen 18 enter the scintillator 13. The scintillator 13 emits fluorescent light (scintillation light) when irradiated by the X-rays. The imaging panel 12 and controller 14 capture the scintillation light in order to acquire an image.

Figure 2A:
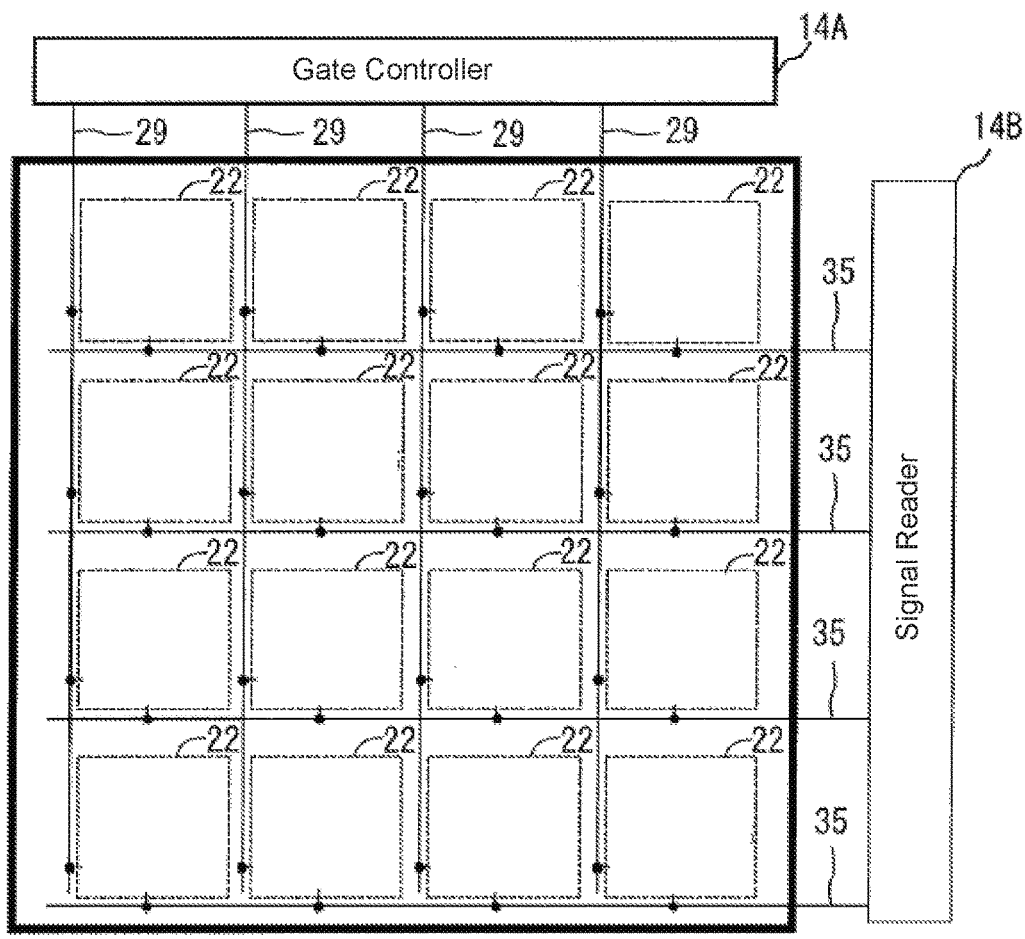
FIG. 2A is a schematic view of the arrangement of a plurality of pixels in the imaging panel.

As shown in FIG. 2A, the imaging panel 12 includes a plurality of pixels 22. As shown in FIG. 2A, the plurality of pixels 22 are arranged in a matrix pattern. In the example shown in FIG. 2A, sixteen pixels 22 are arranged in 4 rows×4 columns. The pixels 22 output signals (light detection signals) that correspond to the intensity of incident scintillation light.

Figure 3:
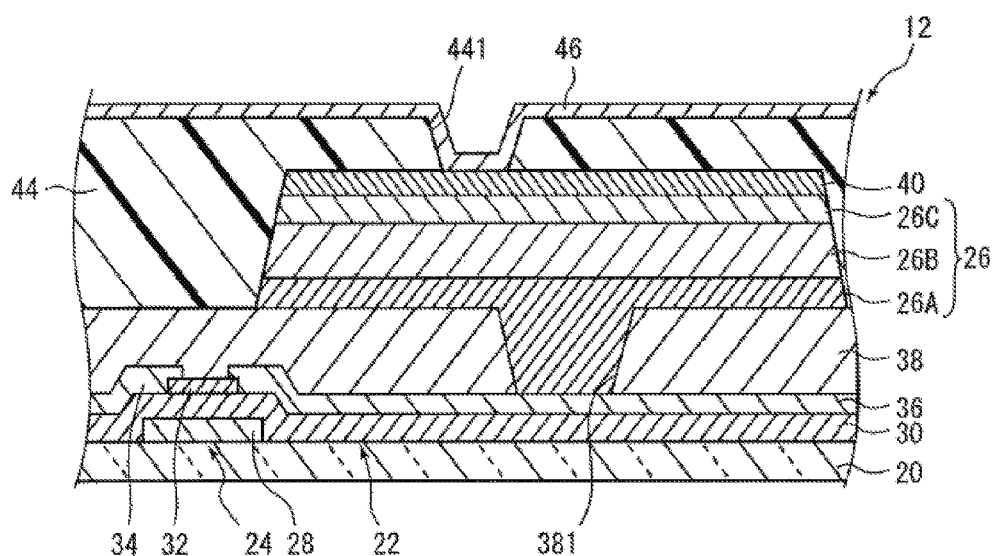
FIG. 3 is a cross-sectional view of FIG. 4 along A-A and shows a cross section of a general configuration of the pixel.

FIG. 3 is a cross-sectional view of a general configuration of one of the pixels 22 of the imaging panel 12. The pixel 22 is formed on a substrate 20 in the imaging panel 12. The substrate 20 has no particular limitations as long as the substrate is an insulating substrate. The substrate 20 may be a glass substrate, for example, or a compound resin substrate. The compound resin may be polyethylene terephthalate (PET), polyethylene naphthalate (PEN), polyether sulfone (PES), an acrylic resin, a polyimide, or the like, for example.

Figure 2B:
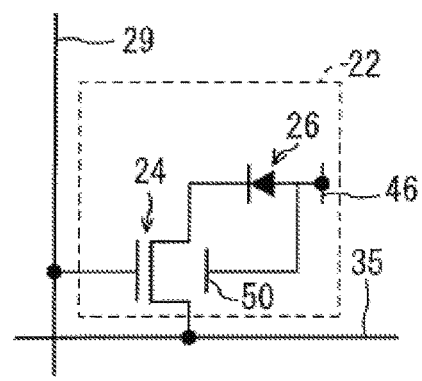
FIG. 2B is an equivalent circuit of a pixel.

As shown in FIG. 2B, the pixel 22 includes a thin film transistor 24, a photodiode 26 as a photoelectric conversion element, and a backgate electrode 50.

As shown in FIG. 3, the thin film transistor 24 includes a gate electrode 28, gate insulating film 30, semiconductor active layer 32, source electrode 34, and drain electrode 36.

Figure 4:
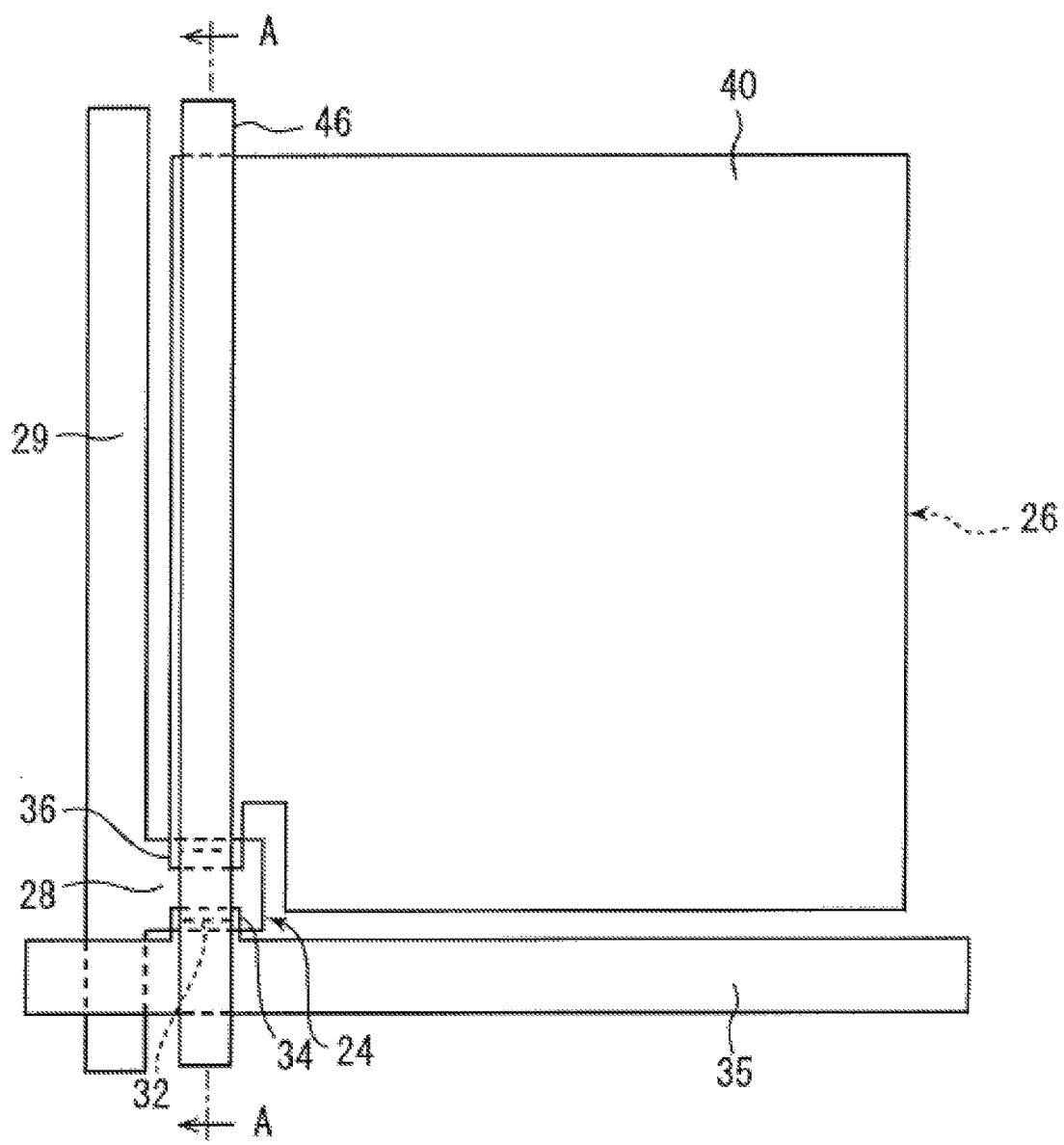
FIG. 4 is a plan view of a general configuration of the pixel.

As shown in FIG. 3, the gate electrode 28 is formed contacting one surface (hereinafter, main surface) of the substrate 20 in the thickness direction. The gate electrode 28 is formed of a metal such as aluminum (Al), tungsten (W), molybdenum (Mo), tantalum (Ta), chromium (Cr), titanium (Ti), or copper (Cu), for example, or alternatively is a nitride of these metals. Alternatively, the gate electrode 28 may be a plurality of metal films layered together, for example. In the present embodiment, the gate electrode 28 has a multilayer structure in which a titanium metal film, aluminum metal film, and titanium metal film are layered together in this order. The gate electrode 28 is formed by using sputtering or the like to form a metal film on the substrate 20 and then patterning this metal film via photolithography, for example. The thickness of the gate electrode 28 is 50 nm to 300 nm, for example. The gate electrode 28 may be constituted by a gate line formed on the substrate 20 and extending in a prescribed direction, or alternatively the gate electrode may be constituted by a portion extending from the gate line in a direction that differs from the prescribed direction. As shown in FIG. 4, in the present embodiment, the gate electrode 28 is constituted by a portion extending from a gate line 29.

As shown in FIG. 3, the gate insulating film 30 is formed on the substrate 20 and covers the gate electrode 28. The gate insulating film 30 includes a silicon nitride film and a silicon oxide film, for example. The silicon nitride film is formed contacting the gate electrode 28 and substrate 20.

The silicon oxide film is formed contacting the silicon nitride film. The thickness of the silicon nitride film is 100 nm to 400 nm, for example. The thickness of the silicon oxide film is 50 nm to 100 nm, for example. The gate insulating film 30 is formed by plasma-enhanced CVD, for example. In order to form a precise insulating film with low gate leakage current at a low temperature, a noble gas element such as argon may be included in the reactive gas and mixed into the insulating film. The gate insulating film 30 may alternatively be constituted by only the silicon oxide film. Instead of a silicon nitride film, the insulating film may be a silicon nitride oxide film ($SiN_xO_y$) (x>y). Instead of a silicon oxide film, the insulating film may be a silicon oxynitride film ($SiO_xN_y$) (x>y).

As shown in FIG. 3, the semiconductor active layer 32 is formed contacting the gate insulating film 30. The semiconductor active layer 32 is an oxide semiconductor. The oxide semiconductor is an oxide containing prescribed proportions of indium (In), gallium (Ga), and zinc (Zn), for example. The oxide semiconductor may be $InGaO_3$ $(ZnO)_5$, magnesium zinc oxide ($Mg_xZn_{1-x}O$), cadmium zinc oxide ($Cd_xZn_{1-x}O$), cadmium oxide (CdO), or an In—Ga—Zn—O amorphous oxide semiconductor (a-IGZO), for example. The oxide semiconductor may be non-crystalline, polycrystalline, or microcrystalline ZnO having a mix of non-crystalline and polycrystalline states, or a material that has had no impurity elements added to this ZnO. The impurity element is one or multiple elements selected from group 1 elements, group 13 elements, group 14 elements, group 15 elements, or group 17 elements. The thickness of the semiconductor active layer 32 is 30 nm to 100 nm, for example. The semiconductor active layer 32 is formed by forming a semiconductor layer via sputtering or the like and then using photolithography to pattern the semiconductor layer, for example. After the semiconductor layer has been formed, or after the semiconductor active layer 32 has been formed, a high-temperature heat treatment (350° C. or greater, for example) may be performed in an environment containing oxygen (e.g., the atmosphere). In such a case, it is possible to reduce oxygen defects in the oxide semiconductor layer.

As shown in FIG. 3, the source electrode 34 and drain electrode 36 are formed contacting the semiconductor active layer 32 and gate insulating film 30. As shown in FIG. 4, the source electrode 34 is connected to the source line 35. The source electrode 34, source line 35, and drain electrode 36 are formed on the same layer. The source electrode 34, source line 35, and drain electrode 36 are formed of a metal such as aluminum (Al), tungsten (W), molybdenum (Mo), tantalum (Ta), chromium (Cr), titanium (Ti), or copper (Cu), for example, or alternatively is a nitride of these metals. The source electrode 34, source line 35, and drain electrode 36 may be a plurality of metal films layered together, for example. In the present embodiment, the source electrode 34, source line 35, and drain electrode 36 have a multilayer structure in which a titanium metal film, aluminum metal film, and titanium metal film are layered together in this order. The thickness of the source electrode 34, source line 35, and drain electrode 36 is 50 nm to 500 nm, for example. The source electrode 34, source line 35, and drain electrode 36 are formed by using sputtering or the like to form a metal film on the semiconductor active layer 32 and gate insulating film 30 and then patterning this metal film via photolithography, for example. The etching when patterning the metal film may be dry etching or may be wet etching. When etching a metal film formed on a substrate with a wide area, it is preferable to use dry etching (anisotropic etching), which has less line width shifts, or namely less variation in line width.

As shown in FIG. 3, the imaging panel 12 further includes an insulating film 38. The insulating film 38 covers the semiconductor active layer 32, source electrode 34, source line 35, and drain electrode 36. The insulating film 38 functions as a passivation film. The insulating film 38 is a silicon oxide film, for example. The insulating film 38 may be a silicon nitride film, or alternatively may be a silicon nitride film and silicon oxide film that have been layered together. The thickness of the insulating film 38 is 50 nm to 300 nm, for example. The insulating film 38 is formed by plasma-enhanced CVD, for example.

After the insulating film 38 has been formed, a heat treatment may be performed at a temperature of approximately 350 degrees. In such a case, it is possible to reduce defects in the insulating film 38.

The insulating film 38 has formed therein a contact hole 381. The contact hole 381 overlaps the drain electrode 36 when seen from a direction perpendicular to the main surface of the substrate 20. The contact hole 381 is formed by photolithography, for example.

As shown in FIG. 3, the photodiode 26 is connected to the drain electrode 36 via the contact hole 381. The entirety of the photodiode 26 overlaps the drain electrode 36 when seen from the direction perpendicular to the main surface of the substrate 20. The photodiode 26 includes an n-type amorphous silicon layer 26A, an intrinsic amorphous silicon layer 26B, and a p-type amorphous silicon layer 26C.

The n-type amorphous silicon layer 26A is made of amorphous silicon that has been doped by an n-type impurity (phosphorous, for example). The n-type amorphous silicon layer 26A is formed contacting the drain electrode 36. The thickness of the n-type amorphous silicon layer 26A is 20 nm to 100 nm, for example.

The intrinsic amorphous silicon layer 26B is made of intrinsic amorphous silicon. The intrinsic amorphous silicon layer 26B is formed contacting the n-type amorphous silicon layer 26A. The thickness of the intrinsic amorphous silicon layer 26B is 200 nm to 2000 nm, for example.

The p-type amorphous silicon layer 26C is made of amorphous silicon that has been doped by a p-type impurity (boron, for example). The p-type amorphous silicon layer 26C is formed contacting the intrinsic amorphous silicon layer 26B. The thickness of the p-type amorphous silicon layer 26C is 10 nm to 50 nm, for example.

The photodiode 26 is formed by plasma-enhanced CVD of the n-type amorphous silicon film, intrinsic amorphous silicon film, and p-type amorphous silicon film in this order, for example. Thereafter, these films are patterned via photolithography. This results in the forming of the photodiode 26.

As shown in FIG. 3, the imaging panel 12 further includes an electrode 40. The electrode 40 is formed contacting the p-type amorphous silicon layer 26C of the photodiode 22. The electrode 40 covers all of the p-type amorphous silicon layer 26. The electrode 40 is a transparent conductive film, for example. The transparent conductive film is indium zinc oxide, for example. The electrode 40 is formed by forming the transparent conductive film via sputtering or the like and then patterning this transparent conductive film via photolithography, for example. The thickness of the electrode 40 is 50 nm to 500 nm, for example.

As shown in FIG. 3, the imaging panel 12 further includes a planarizing film 44. The planarizing film 44 is made of a photosensitive resin, for example. The planarizing film 44 covers the insulating film 42 and electrode 40. The thickness of the planarizing film 44 is 1000 nm to 4000 nm, for example. The planarizing film 44 is formed by spin coating, slit coating, or the like, and then a thermal treatment thereafter in a 150 to 250 degree atmosphere, for example. The thermal treatment temperature when curing the planarizing film 44 differs depending on the material of the planarizing film 44. The planarizing film 44 has formed therein a contact hole 441. The contact hole 441 overlaps the electrode 40 when seen from the direction perpendicular to the main surface of the substrate 20. The contact hole 441 is formed by photolithography, for example.

As shown in FIGS. 3 and 4, the imaging panel 12 further includes a wiring line 46. The wiring line 46 is formed on the planarizing film 44. As shown in FIG. 4, the wiring line 46 extends parallel to the source line 35. The wiring line 46 overlaps the semiconductor active layer 32 when seen from the direction perpendicular to the main surface of the substrate 20. As shown in FIG. 4, in the present embodiment, the wiring line 46 overlaps the portion of the semiconductor active layer 32 not contacting the source electrode 34 and drain electrode 36 when seen from the direction perpendicular to the main surface of the substrate 20. As shown in FIG. 4, in the present embodiment, the wiring line 46 overlaps the portion of the semiconductor active layer 32 overlapping the gate electrode 28 when seen from the direction perpendicular to the main surface of the substrate 20. As shown in FIG. 4, the wiring line 46 overlaps the electrode 40 when seen from the direction perpendicular to the main surface of the substrate 20. The wiring line 46 overlaps the gate electrode 28 when seen from the direction perpendicular to the main surface of the substrate 20. In other words, a portion of the wiring line 46, or specifically, the portion overlapping the gate electrode 28 when viewed from the direction perpendicular to the main surface of the substrate 20, functions as the backgate electrode 50. The wiring line 46 is made of a metal such as aluminum (Al), tungsten (W), molybdenum (Mo), tantalum (Ta), chromium (Cr), titanium (Ti), or copper (Cu), or is an alloy of these metals or a metal nitride of these, for example. The wiring line 46 may be a transparent conductive film, for example. The transparent conductive film is indium zinc oxide, for example. The wiring line 46 contacts the electrode 40 via the contact hole 441. The thickness of the wiring line 46 is 50 nm to 500 nm, for example. The wiring line 46 is formed by forming a conductive film via sputtering or the like and then patterning this conductive film via photolithography, for example.

As shown in FIG. 1, the controller 14 includes a gate controller 14A, signal reader 14B, image processor 14C, bias controller 14D, X-ray controller 14E, and timing controller 14F. In FIG. 1, the controller 14 is provided separately from the imaging panel 12, but alternatively, a portion or all of the controller 14 may be provided in the imaging panel 12.

As shown in FIG. 2A, the gate controller 14A is connected to a plurality of gate lines 29. Several of the plurality of pixels 22 are connected to each of the gate lines 29. In the example shown in FIG. 2A, four of the pixels 22 are connected to each of the gate lines 29. The gate controller 14A selects one gate line 29 from the plurality of gate lines 29 based on the control signal from the timing controller 14F. The gate controller 14A applies, via the selected gate line 29, a prescribed gate voltage to the thin film transistor 24 of the pixel 22 connected to the corresponding gate line 29 (see FIG. 2B).

As shown in FIG. 2A, the signal reader 14B is connected to the plurality of source lines 35. Several of the plurality of pixels 22 are connected to each of the source lines 35. In the example shown in FIG. 2A, four of the pixels 22 are connected to each of the source lines 35. The signal reader 14B selects one source line 35 from the plurality of source lines 35 based on the control signal from the timing controller 14F. The signal reader 14B reads out light detection signals via the selected source line 35. The light detection signals correspond to the electric charge generated by the photodiode 26 when scintillation light enters the photodiode 26. In other words, the magnitude of the light detection signal changes in accordance with the amount of electrical charge generated by the photodiode 26. The pixel 22 for which the light detection signal is read out is connected to the source line 35 selected by the signal reader 14B and connected to the gate line 29 selected by the gate controller 14A. The signal reader 14B generates image signals based on the read out light detection signals and outputs the result to the image processor 14C.

The image processor 14C generates images based on the image signals output from the signal reader 14B.

The bias controller 14D is connected to the wiring line 46. The bias controller 14D applies a prescribed voltage to the wiring line 46 based on the control signal from the timing controller 14F. This applies a bias voltage to the photodiode 26. This results in the expansion of a depletion layer in the photodiode 26.

The X-ray controller 14E controls the radiation of X-rays by the X-ray source 16 based on the control signal from the timing controller 14F.

The timing controller 14F controls the operation timing of the gate controller 14A, signal reader 14B, bias controller 14D, and X-ray controller 14E.

In the X-ray imaging system 10, the X-rays radiated from the X-ray source 16 irradiate the scintillator 13 via the specimen 18. The X-rays that have irradiated the scintillator 13 are converted to scintillation light. The scintillation light enters the photodiode 26. This generates a light detection signal. At such time, the thin film transistor 24 turns ON, and the light detection signal is read out. An image signal is generated based on the light detection signal that is read out. An image is generated based on the generated image signal.

Figure 5:
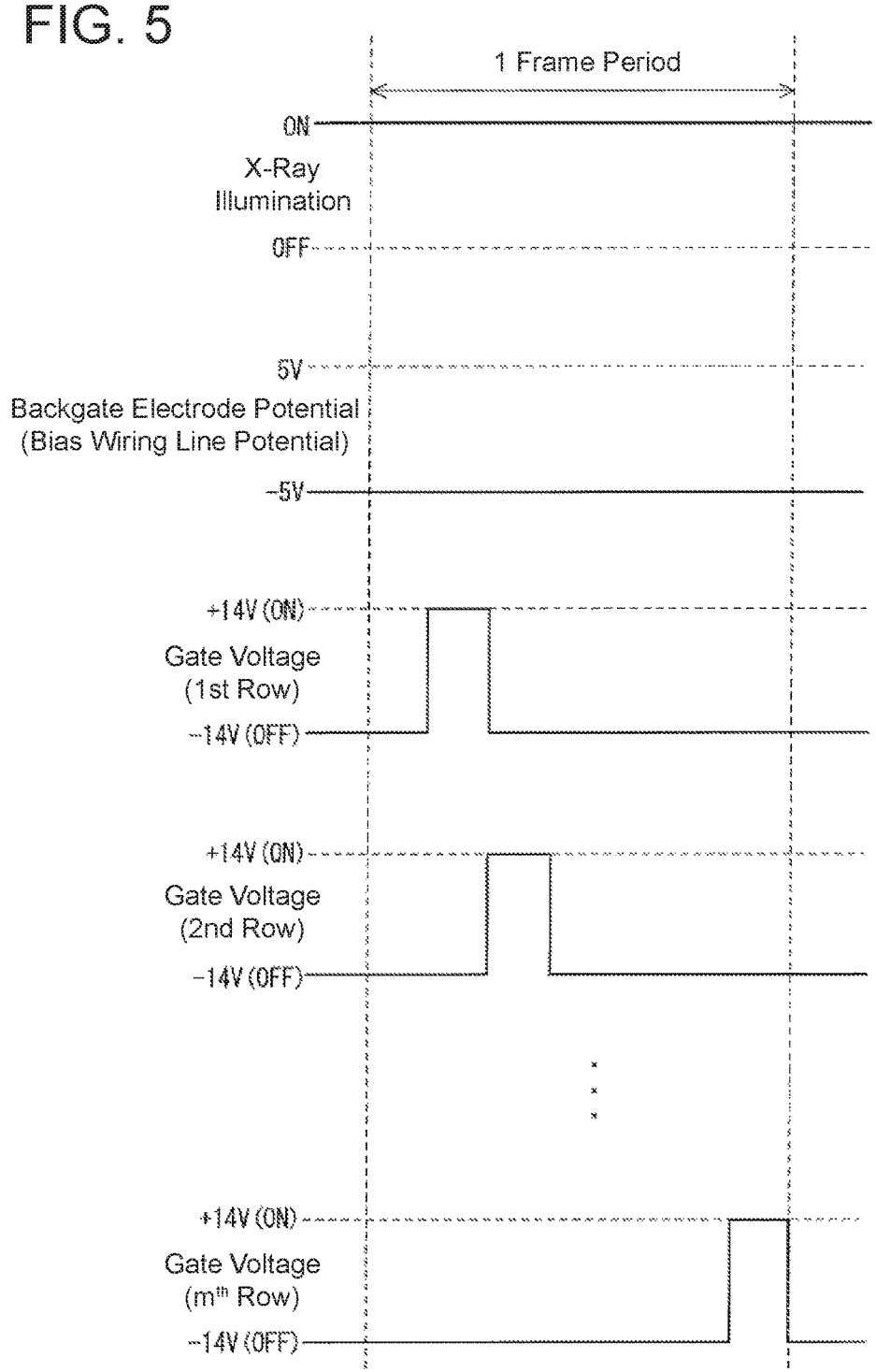
FIG. 5 is a timing chart for Embodiment 1 showing the relationship between X-ray radiation period and potential of the respective gate electrodes.

As shown in FIG. 5, in the X-ray imaging system 10, during the radiation period when X-rays are radiated, gate voltages are sequentially applied to the plurality of gate lines 29 and a negative charge is applied to the wiring line 46.

The negative voltage being applied to the wiring line 46 shifts the threshold of the thin film transistor 24 in the plus direction. Thus, it is possible to stabilize the operation of the thin film transistor 24. The reason for this is as follows.

In order to reduce OFF current (leakage current) of the thin film transistor 24, a negative charge is applied to the gate electrode 28 when the thin film transistor 24 is to be turned OFF. If the period during which the negative charge is applied is long, the threshold voltage of the thin film transistor 24 shifts in the minus direction. As a countermeasure, the threshold voltage is shifted in the plus direction beforehand, for example. Thus, even if the threshold voltage shifts in the minus direction, the threshold voltage will not likely reach minimum value. As a result, it is possible to stabilize the operation of the thin film transistor 24.

In the X-ray imaging system 10, the wiring line 46 (backgate electrode 50) can shield the semiconductor active layer 32 from light. Thus, it is harder for scintillation light to enter the semiconductor active layer 32. This results in the characteristics of the thin film transistor 24 being unsusceptible to deterioration. Accordingly, it is possible to stabilize the operation of the thin film transistor 24.

Embodiment 2

Figure 6:
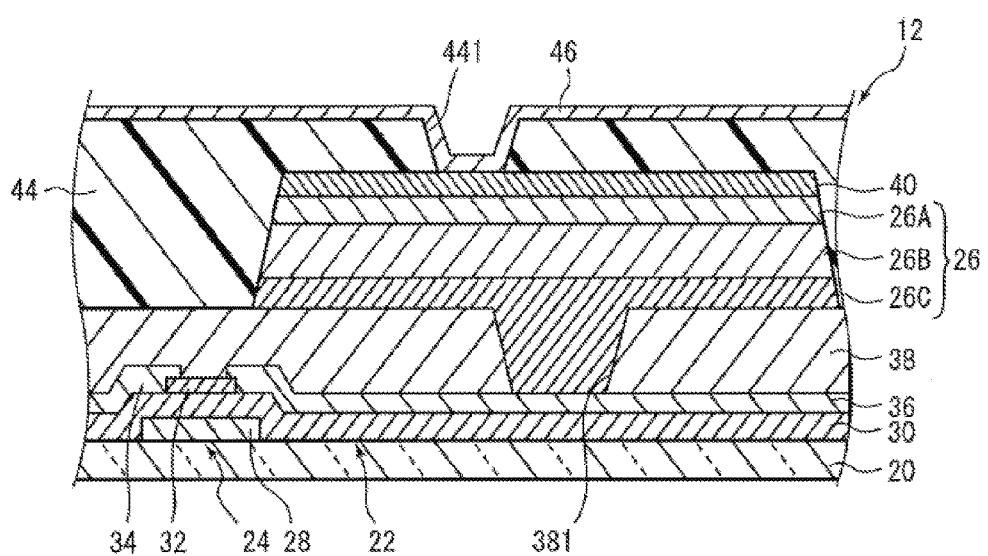
FIG. 6 is a cross-sectional view showing a schematic configuration of a pixel according to Embodiment 2 of the present invention.
Figure 7:
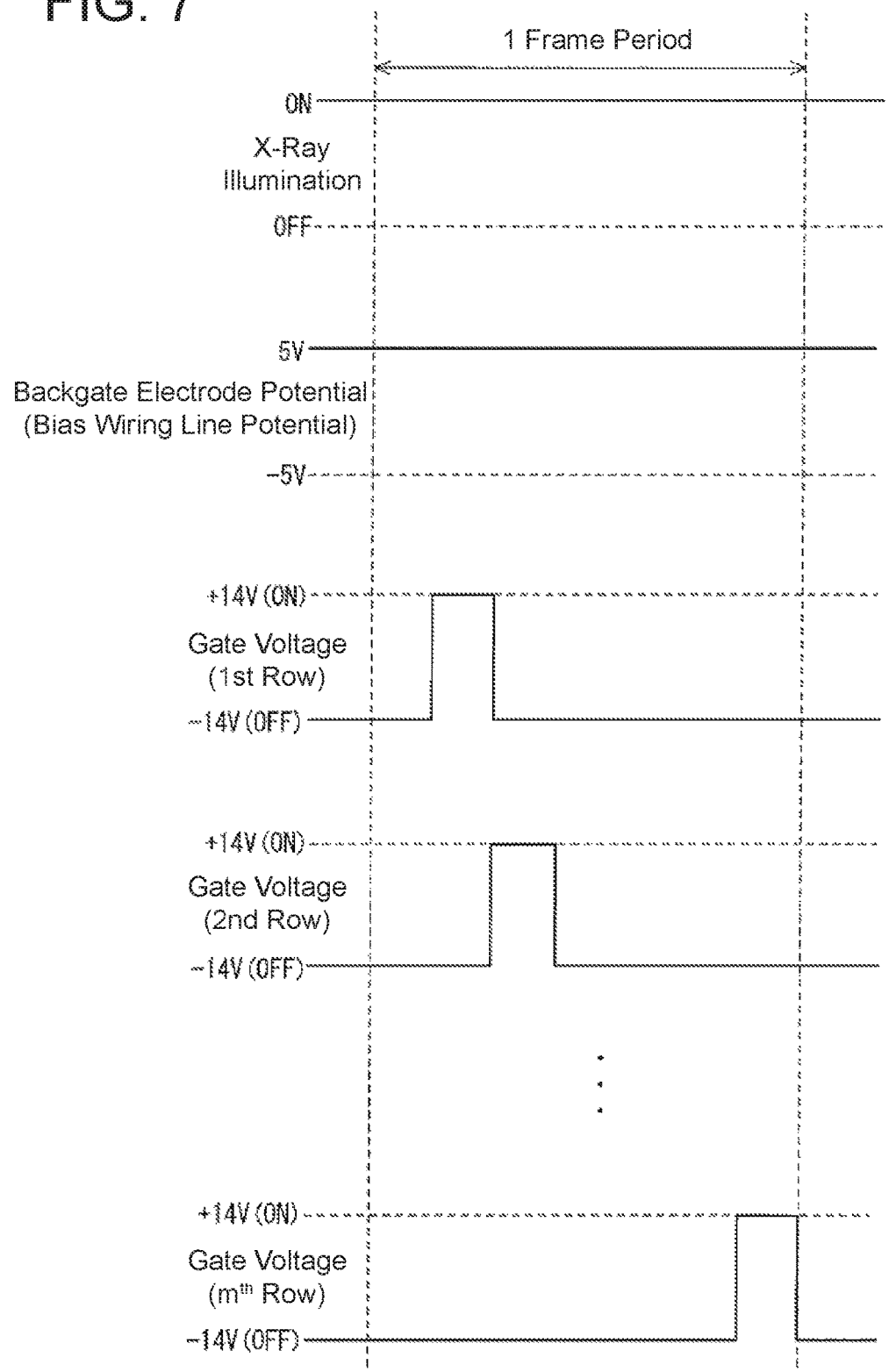
FIG. 7 is a timing chart for Embodiment 2 showing the relationship between X-ray radiation period and potential of the respective gate electrodes.

Next, Embodiment 2 of the present invention will be described with reference to FIGS. 6 and 7. As shown in FIG. 6, in the present embodiment as compared to Embodiment 1, the p-type amorphous silicon layer 26C is contacting the drain electrode 36 and intrinsic amorphous silicon layer 26B. The n-type amorphous silicon layer 26A contacts the intrinsic amorphous silicon layer 26B and the electrode 40. As shown in FIG. 7, during the radiation period when X-rays are radiated, gate voltages are sequentially applied to the plurality of gate lines 29 and a positive voltage is applied to the wiring line 46.

In the present embodiment, during the period when the light detection signal is read out, a positive voltage is applied to the wiring line 46. This shifts the threshold of the thin film transistor 24 in the minus direction. Thus, it is possible to reduce the operating voltage of the thin film transistor 24 (the voltage applied to the gate electrode 28).

Embodiment 3

Figure 8:
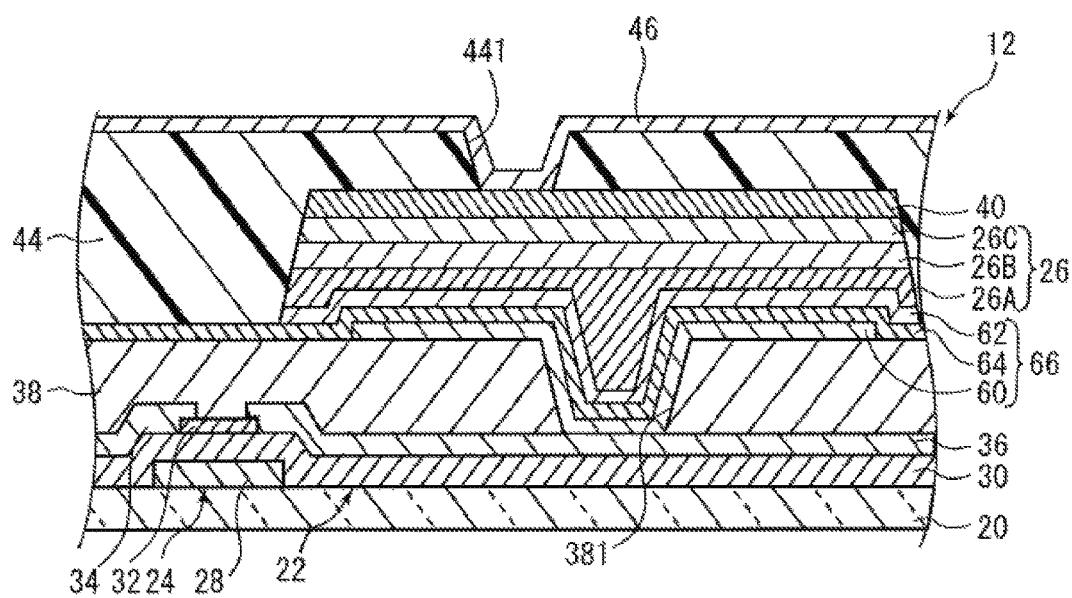
FIG. 8 is a cross-sectional view showing a schematic configuration of a pixel according to Embodiment 3 of the present invention.
Figure 9:
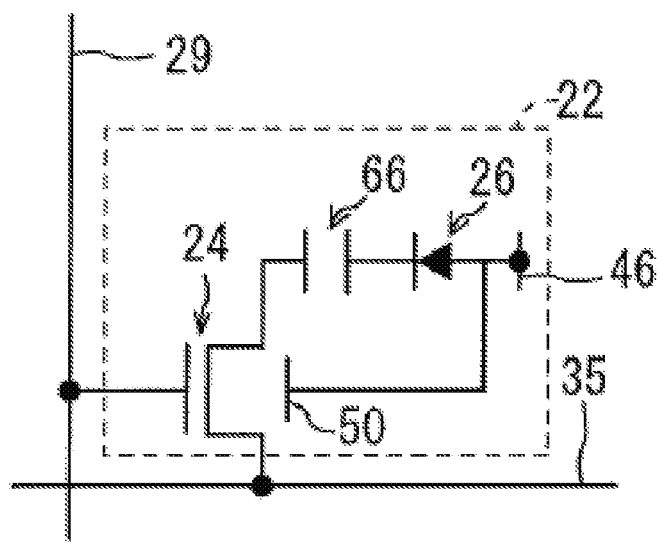
FIG. 9 is an equivalent circuit of a pixel in Embodiment 3.

Next, Embodiment 3 of the present invention will be described with reference to FIGS. 8, 9, and 10. As shown in FIG. 8, the imaging panel 12 includes an electrode 60, electrode 62, and insulating film 64.

The electrode 60 is formed contacting the insulating film 38. The electrode 60 contacts the drain electrode 36 via the contact hole 381. The electrode 60 is made of a metal such as aluminum (Al), tungsten (W), molybdenum (Mo), tantalum (Ta), chromium (Cr), titanium (Ti), or copper (Cu), or is an alloy of these metals or a metal nitride of these, for example. The electrode 60 may be a transparent conductive film. The transparent conductive film is indium zinc oxide, for example. The electrode 60 overlaps the photodiode 26 when seen from the direction perpendicular to the main surface of the substrate 20. The thickness of the electrode 60 is 50 nm to 200 nm, for example. The electrode 60 is formed by forming a conductive film via sputtering or the like and then patterning this conductive film via photolithography, for example.

The insulating film 64 covers the insulating film 38 and electrode 60. The insulating film 64 is a silicon nitride film, for example. The insulating film 64 may be a silicon oxide film, or alternatively may be a silicon nitride film and silicon oxide film that have been layered together. The thickness of the insulating film 64 is approximately 50 nm to 300 nm, for example. The insulating film 64 is formed by plasma-enhanced CVD, for example. The planarizing film 44 is formed contacting the insulating film 64.

The electrode 62 is formed contacting the insulating film 64. The n-type amorphous silicon layer 26A is formed contacting the electrode 62. In other words, the photodiode 26 is formed contacting the electrode 62. The electrode 62 is made of a metal such as aluminum (Al), tungsten (W), molybdenum (Mo), tantalum (Ta), chromium (Cr), titanium (Ti), or copper (Cu), or is an alloy of these metals or a metal nitride of these, for example. The electrode 62 may be a transparent conductive film. The transparent conductive film is indium zinc oxide, for example. The electrode 62 overlaps the electrode 60 when seen from the direction perpendicular to the main surface of the substrate 20. The thickness of the electrode 62 is 50 nm to 200 nm, for example. The electrode 62 is formed by forming a conductive film via sputtering or the like and then patterning this conductive film via photolithography, for example.

A capacitor 66 is formed by the electrode 60, electrode 62, and the portion of the insulating film 64 positioned between these electrodes 60 and 62. As shown in FIG. 9, the capacitor 66 is connected in series to the photodiode 26. The capacitor 66 is connected to the drain electrode 36.

The operation of the X-ray imaging system of the present embodiment will be explained with reference to FIG. 10.

First, the bias controller 14D applies a positive voltage to the wiring line 46 for a prescribed period (storage period). This stores electric charge in the capacitor 66 via the photodiode 26.

After the prescribed period has passed, the bias controller 14D applies a negative voltage to the wiring line 46. This applies a reverse bias voltage to the photodiode 26. As a result, the electric charge remains stored in the capacitor 66.

When the voltage applied to the wiring line 46 switches from positive to negative, the X-ray controller 14E causes the X-ray source 16 to operate and radiate X-rays for a prescribed period (radiation period). After the prescribed period has passed, the X-ray controller 14E causes the X-ray source 16 to operate and ends the X-ray radiation.

The radiated X-rays enter the scintillator 13 via the specimen 18. The X-rays that have entered the scintillator 13 are converted to scintillation light. The scintillation light enters the photodiode 26. At such time, the electric charge stored in the capacitor 66 flows out via the photodiode 26. In other words, when scintillation light has been detected by the photodiode 26, the amount of electric charge stored in the capacitor 66 decreases. In other words, the electric charge stored in the capacitor 66 corresponds to the intensity of the scintillation light detected by the photodiode 26.

Thereafter, the gate controller 14A and signal reader 14B read out the light detection signal. In other words, the electric charge stored in the capacitor 66 is read out. The signal reader 14B generates image signals based on the light detection signals that have been read out. The image processor 14C generates images based on the image signals that have been generated.

Figure 10:
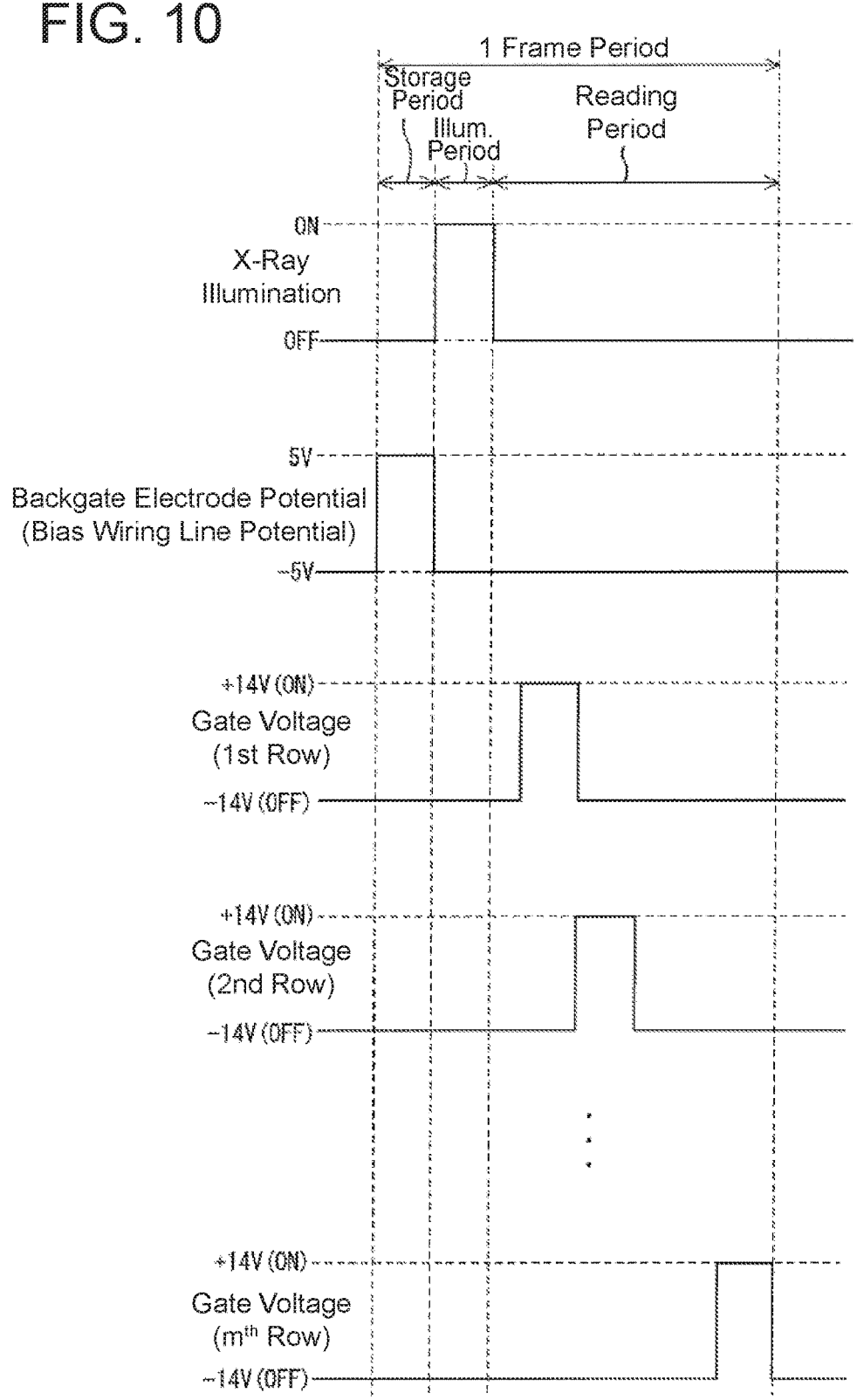
FIG. 10 is a timing chart for Embodiment 3 showing the relationship between X-ray radiation period and potential of the respective gate electrodes.

In the present embodiment, as shown in FIG. 10, the radiation period when X-rays are radiated is separate from the reading period when the light detection signals are read out. In other words, the light detection signals are read out when X-rays are not being radiated. Namely, X-rays are radiated intermittently. Thus, it is possible to reduce the amount of exposure of the specimen 18.

Furthermore, in the present embodiment, the capacitor 66 is connected in series to the photodiode 26. Thus, when the electric charged stored in the capacitor 66 is read out, it is possible for the photodiode 26 to prevent the electric charge from leaking. This makes it possible to improve the quality of the images that are generated based on the electric charge that is read out.

Embodiment 4

Figure 11:
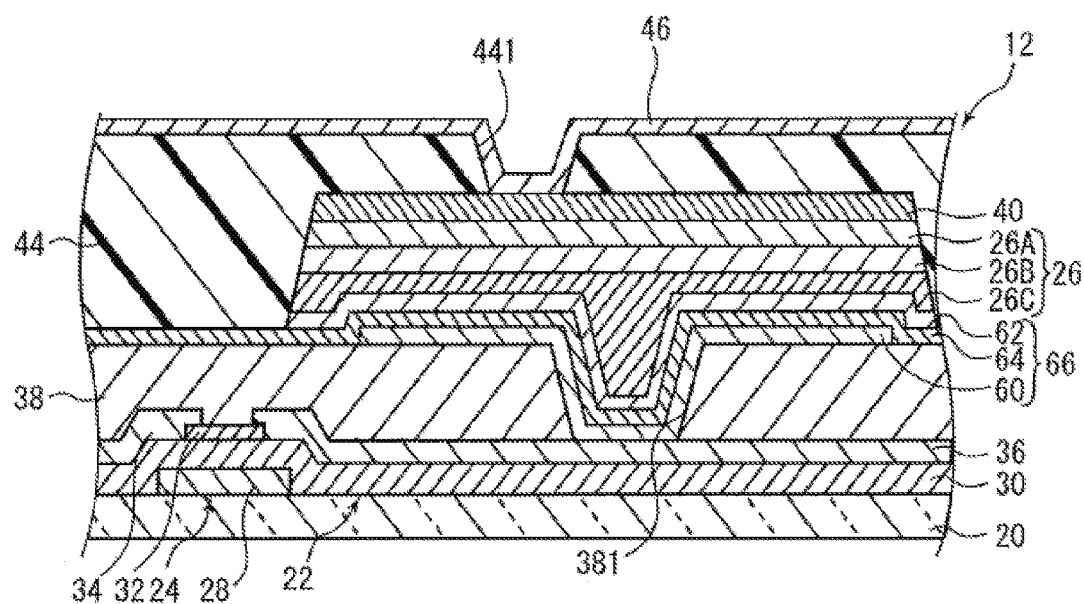
FIG. 11 is a cross-sectional view showing a schematic configuration of a pixel according to Embodiment 4 of the present invention.
Figure 12:
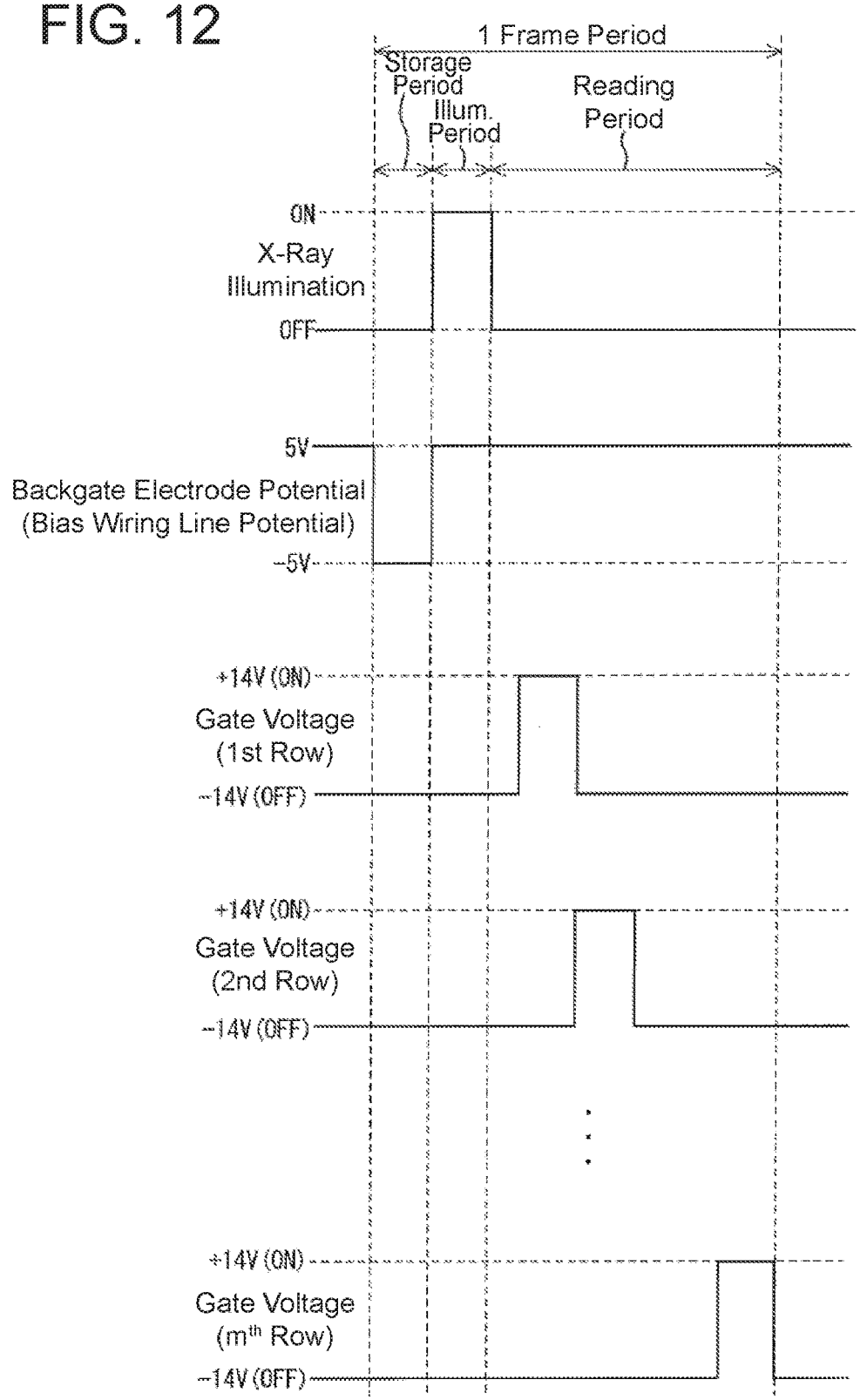
FIG. 12 is a timing chart for Embodiment 4 showing the relationship between X-ray radiation period and potential of the respective gate electrodes.

Embodiment 4 of the present invention will be described with reference to FIGS. 11 and 12. As shown in FIG. 11, in the present embodiment as compared to Embodiment 3, the p-type amorphous silicon layer 26C is contacting the drain electrode 36 and intrinsic amorphous silicon layer 26B. The n-type amorphous silicon layer 26A contacts the intrinsic amorphous silicon layer 26B and the electrode 40.

The operation of the X-ray imaging system of the present embodiment will be explained with reference to FIG. 12.

First, the bias controller 14D applies a negative voltage to the wiring line 46 for a prescribed period (storage period). This stores electric charge in the capacitor 66 via the photodiode 26.

After the prescribed period has passed, the bias controller 14D applies a positive voltage to the wiring line 46. This applies a reverse bias voltage to the photodiode 26. As a result, the electric charge remains stored in the capacitor 66.

When the voltage applied to the wiring line 46 switches from negative to positive, the X-ray controller 14E causes the X-ray source 16 to operate and radiate X-rays for a prescribed period (radiation period). After the prescribed period has passed, the X-ray controller 14E causes the X-ray source 16 to operate and ends the X-ray radiation.

The radiated X-rays enter the scintillator 13 via the specimen 18. The X-rays that have entered the scintillator 13 are converted to scintillation light. The scintillation light enters the photodiode 26. At such time, the electric charge stored in the capacitor 66 flows out via the photodiode 26. In other words, when scintillation light has been detected by the photodiode 26, the amount of electric charge stored in the capacitor 66 decreases. In other words, the electric charge stored in the capacitor 66 corresponds to the intensity of the scintillation light detected by the photodiode 26.

Thereafter, the gate controller 14A and signal reader 14B read out the light detection signal (reading period). In other words, the electric charge stored in the capacitor 66 is read out. The signal reader 14B generates image signals based on the light detection signals that have been read out. The image processor 14C generates images based on the image signals that have been generated.

In the present embodiment, during the reading period, a positive voltage is applied to the wiring line 46. This shifts the threshold of the thin film transistor 24 in the minus direction. Thus, it is possible to reduce the operating voltage of the thin film transistor 24 (the voltage applied to the gate electrode 28).

The embodiments of the present invention have been described above. However, these are merely examples, and the present invention is not at all limited by the embodiments described above.

What is claimed is:

1. An imaging panel for generating an image in accordance with scintillation light obtained from X-rays that have passed through a specimen, the imaging panel comprising:
    a substrate;
    a thin film transistor on the substrate;
    a photoelectric conversion element connecting to the thin film transistor and receiving the scintillation light; and
    a bias wiring line connecting to the photoelectric conversion element and applying a reverse bias voltage to the photoelectric conversion element,
    wherein the thin film transistor includes:
        a semiconductor active layer; and
        a gate electrode between the substrate and semiconductor active layer, and
    wherein the bias wiring line includes a section that overlaps the gate electrode and the semiconductor active layer as seen from a radiation direction of the scintillation light such that the reverse bias voltage is capacitively coupled to the semiconductor active layer thereunder.

2. The imaging panel according to claim 1,
    wherein the thin film transistor includes a drain electrode connecting to the photoelectric conversion element,
    wherein the photoelectric conversion element includes:
        an n-type semiconductor layer contacting the drain electrode;
        an intrinsic semiconductor layer contacting the n-type semiconductor layer; and
        a p-type semiconductor layer contacting the intrinsic semiconductor layer, and
    wherein the bias wiring line makes a potential of the p-type semiconductor layer lower than a potential of the n-type semiconductor layer.

3. The imaging panel according to claim 1,
    wherein the thin film transistor includes a drain electrode connecting to the photoelectric conversion element,
    wherein the photoelectric conversion element includes:
        a p-type semiconductor layer contacting the drain electrode;
        an intrinsic semiconductor layer contacting the p-type semiconductor layer; and
        an n-type semiconductor layer contacting the intrinsic semiconductor layer,
    wherein the bias wiring line makes a potential of the n-type semiconductor layer higher than a potential of the p-type semiconductor layer.

4. The imaging panel according to claim 1, wherein the semiconductor active layer is made of an oxide semiconductor.

5. The imaging panel according to claim 4, wherein the oxide semiconductor is an oxide containing prescribed proportions of indium (In), gallium (Ga), and zinc (Zn).

6. The imaging panel according to claim 4,
    wherein the thin film transistor further includes:
        a first insulating film between the gate electrode and the semiconductor active layer and covering the gate electrode; and
        a second insulating film covering the semiconductor active layer, and
    wherein the first insulating film and the second insulating film include a silicon oxide film contacting the semiconductor active layer.

7. An X-ray imaging system, comprising:
    the imaging panel according to claim 1;
    an X-ray source; and
    a scintillator between the X-ray source and the imaging panel.

8. The imaging panel according to claim 2, wherein the semiconductor active layer is made of an oxide semiconductor.

9. The imaging panel according to claim 3, wherein the semiconductor active layer is made of an oxide semiconductor.

10. The imaging panel according to claim 5,
    wherein the thin film transistor further includes:
        a first insulating film between the gate electrode and the semiconductor active layer and covering the gate electrode; and
        a second insulating film covering the semiconductor active layer, and
    wherein the first insulating film and the second insulating film include a silicon oxide film contacting the semiconductor active layer.

11. The imaging panel according to claim 8,
    wherein the thin film transistor further includes:
        a first insulating film between the gate electrode and the semiconductor active layer and covering the gate electrode; and
        a second insulating film covering the semiconductor active layer, and wherein the first insulating film and the second insulating film include a silicon oxide film contacting the semiconductor active layer.

12. The imaging panel according to claim 9,
wherein the thin film transistor further includes:
   a first insulating film between the gate electrode and the semiconductor active layer and covering the gate electrode; and
   a second insulating film covering the semiconductor active layer, and
wherein the first insulating film and the second insulating film include a silicon oxide film contacting the semiconductor active layer.

* * * * *